April 26, 1966 R. V. LINDQUIST ...ant Pat. 2,627
ROSE PLANT
Filed April 5, 1965
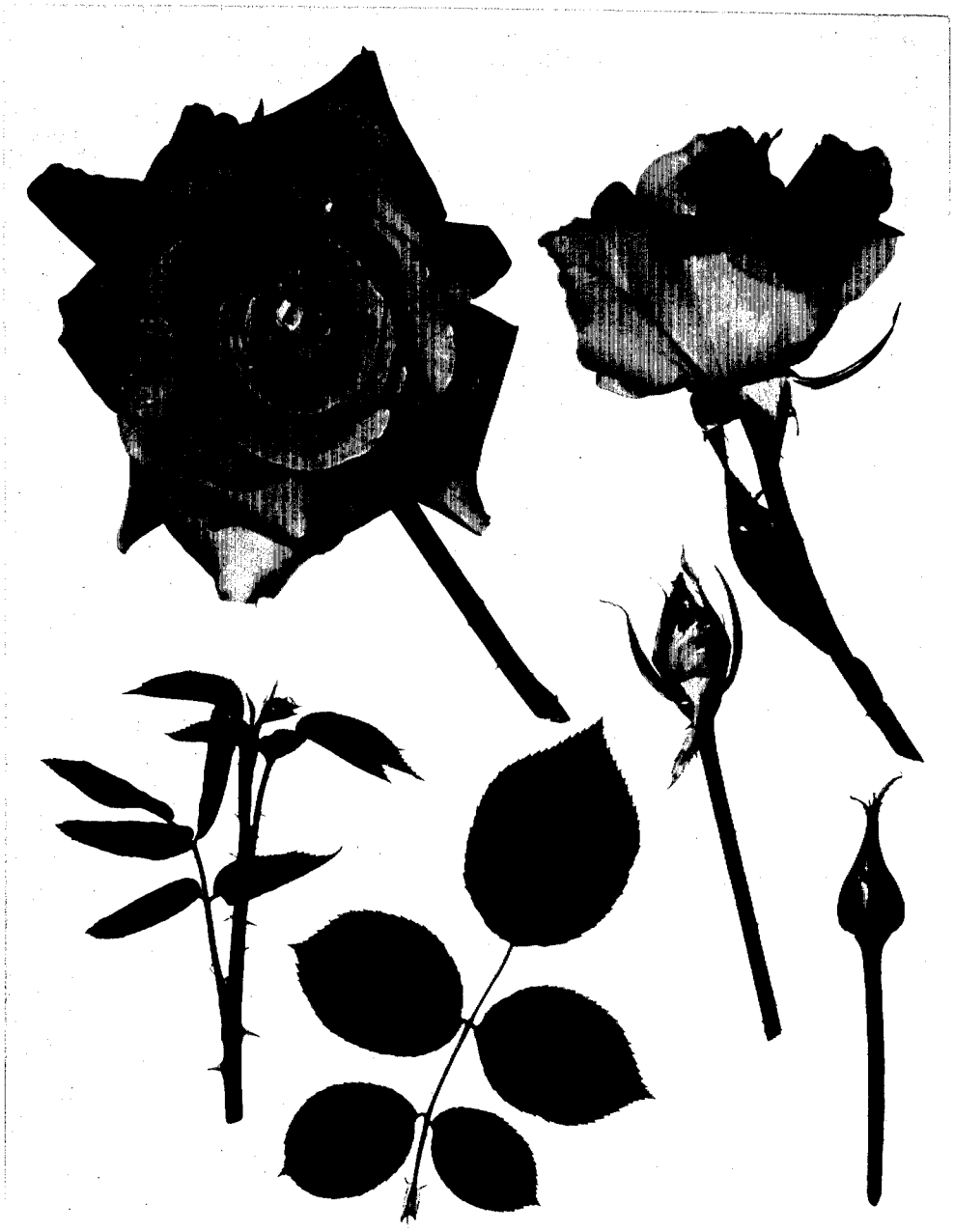
Inventor.
Robert V. Lindquist
By: Robb & Robb
Attorneys.

United States Patent Office

Plant Pat. 2,627
Patented Apr. 26, 1966

2,627
ROSE PLANT

Robert V. Lindquist, Hemet, Calif., assignor to Hemet Wholesale, Hemet, Calif., a partnership Filed Apr. 5, 1965, Ser. No. 445,810
1 Claim. (Cl. Plt.—20)

The present invention relates to a new and distinct variety of rose plant of the hybrid tea class, which was originated by me by crossing an unnamed and unpatended seedling of "Charlotte Armstrong" (Plant Patent No. 355) × "Floradora" (unpatented) with the variety "Nocturne" (Plant Patent No. 713).

As the result of this breeding, I have produced a new and improved rose variety which is particularly characterized as to novelty by the following unique combination of characteristics which are outstanding therein and which distinguish it from its parents, as well as from all other varieties of which I am aware:

(1) Above average vigor;
(2) A uniform and upright habit of growth; and
(3) A unique Rose Red general color tonality of the flowers, popularly described as cherry red.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as (W)) and Ridgway's Color Standards and Nomenclature (hereinafter abbreviated as (R)), as indicated, except where general color terms of ordinary dictionary significance are obvious:

Type: Hardy; tall; bush; outdoor; seedling; for cut flowers and for garden decoration.

Class: Hydrid tea.

Breeding: Seedling.

*Seed parent.*—An unnamed seedling of "Charlotte Armstrong" × "Floradora."

*Pollen parent.*—"Nocturne."

Propagation: Holds its distinguishing characteristics through succeeding propagations by budding.

*Flower*

Locality where grown and observed: Hemet, California.

Flowers borne: Usually singly to stem; on strong stems ranging from medium length to long.

Quantity of bloom: Free, both outdoors and in greenhouse.

Continuity: Continuous during growing season.

Fragrance: Moderate. Nature—nutty.

Bud:

*Peduncle.*—Long; average caliper; erect; almost smooth; some gland-tipped cilia; few prickles. Color—near Spinach Green, Plate 0960/1, page 187 (W).

*Before calyx breaks.*—Size—medium. Form—medium length; pointed; with a conspicuous neck; with foliaceous appendages, tomentum, few gland-tipped cilia, and usually with slender bristle-like foliaceous parts extending beyond the tip of the bud equal to ½ or more of its length.

*As calyx breaks.*—Color—near Chrysanthemum Crimson, Plate 824, page 169 (W).

*Sepals.*—Inner surface—with fine, wooly tomentum. Margins—foliaceous and lined with gland-tipped cilia and hairs.

*As first petal opens.*—Size—average. Form—medium length; urn-shaped. Color—outside—near Rose Red, Plate 724, page 158 (W), with small base of near Empire Yellow, Plate 603/1, page 66 (W); inside—near Rose Red, Plate 724, page 158 (W) with small base of near Empire Yellow, Plate 603/1, page 66 (W).

*Opening.*—Opens up well.

Bloom:

*Size (when fully open).*—Large; from 5 inches to 6 inches.

*Petalage.*—Double; from 30 to 35 petals, plus 6 to 8 petaloids; arranged irregularly.

*Form.*—Cupped at first, but becoming from cupped to high-centered globular; petals being at first somewhat loosely cupped, with tips reflexed and rolled outward, but becoming more loosely cupped, with tips reflexed and rolled outward later at maturity.

Petals:

*Texture.*—Medium thickness.

*Appearance.* — Inside — satiny. Outside — slightly shiny.

*Shape.*—Outside—round, with apex pointed. Intermediate—round, with apex pointed. Inside—nearly round, with apex pointed, and some with one notch.

This description of a newly opened flower was made from a rose grown in a greenhouse during the month of May at Hemet, California:

*Color.*—Outer petal—outside surface—near Rose Red, Plate 724, page 158 (W), with small base of near Empire Yellow, Plate 603/1, page 66 (W); inside surface—near Rose Red, Plate 724, page 158 (W), with some petals having a White streak in the center extending about ½ the petal length, and with small base of near Empire Yellow, Plate 603/1 (W). Intermediate petal—outside surface—near Rose Red, Plate 724, page 158 (W), with small base near Empire Yellow, Plate 603/1, page 66 (W); inside surface—near Rose Red, Plate 724, page 158 (W), with small base near Empire Yellow, Plate 603/1, page 66 (W). Inner petal—outside surface—near Rose Red, plate 724, page 158 (W), with small base of near Empire Yellow, Plate 603/1, page 66 (W); inside surface—near Rose Red, Plate 724, page 158 (W), with small base of near Empire Yellow, Plate 603/1, page 66 (W).

This description was made from a rose that was open for three days in a greenhouse during the month of May at Hemet, California:

*Color.*—Outer petal—outside surface—near China Rose, Plate 024, page 111 (W), with small base of near Empire Yellow, Plate 603/3, page 66 (W); inside surface—near Rose Red, Plate 724, page 158 (W), with some petals having a White streak in the center extending about half the petal length, and with small base of near Empire Yellow, Plate 603/3, page 66 (W). Inner petal—outside surface—near China Rose, Plate 024/1, page 111 (W), with small base of near Empire Yellow, Plate 603/1, page 66 (W); inside surface—near Rose Red, Plate 724/3, page 158 (W), with some petals having a White streak in the center extending about ½ the petal length, and with small base of near Empire Yellow, Plate 603/1, page 66 (W).

*General color effect.*—Newly opened flower—Dark Rose Red. Three days open—lighter shades of Rose Red.

*Behavior.*—Drop off cleanly.

*Flower longevity.*—On bush in garden—4 or 5 days in May. Cut roses grown outdoors and kept at living room temperatures—4 or 5 days in May. Cut roses grown in greenhouse and kept at living room temperatures—4 or 5 days in May.

*Reproductive organs*

Stamens: Average number; arranged regularly about pistils.

Filaments: From medium length to long; most with anthers.

Anthers: Medium size; all open approximately at once.

*Color.*—Upper side—near Clay color, Plate XXIX (R). Under side—near Cinnamon-Buff, Plate XXIX (R).

Pollen: Somewhat sparse. Color—near Yellow Ocher, Plate XV (R).

Pistils: Many; approximately 110 in number.

Styles: Moderately even; from average length to long; average caliper; somewhat bunched.

Stigma: Color—near Pale Pinkish Buff, Plate XXIX (R).

Ovaries: Usually all enclosed in calyx.

Hips: Average length; pear-shaped; some seed protruding from top of hip; moderately smooth; walls thick and fleshy. Color—near Spanish Orange, Plate 010, page 103 (W).

Sepals: Falling soon; long; spear-shaped; recurved.

*Color.*—Inside—near Light Grape Green, Plate XLI (R). Outside—near Lettuce Green, Plate V (R).

Seeds: Few (from 10 to 15 in number); from medium size to large.

*Plant*

Foliage:

*Leaves.*—Compound of usually 5–7 leaflets; normally medium size; from moderately heavy to somewhat leathery and semi-glossy.

*Leaflets.* — Shape — oval, with apex mucronate. Base—round. Margin—irregularly serrate.

*Color.*—Mature—upper surface—near Deep Dull Yellow-Green (2), Plate XXXII (R); under surface—near Deep Dull Yellow Green (1), Plate XXXII (R). Young—upper surface—near Spinach Green, Plate 0960/2, page 187 (W); under surface—near Spinach Green, Plate 0960/3, page 187 (W).

*Rachis (the supporting stem of the compound leaf).*—Average size. Upper side—grooved; with few stipitate glands on edges. Under side—moderately prickly; with stipitate glands.

*Stipules.*—Medium length; narrow; with short points turning out at an angle of more than 45°.

*Disease resistance.*—Better than average resistance to mildew, as determined by comparison with other varieties grown under comparable cultural conditions at Hemet, California.

Growth:

*Habit.*—Upright; moderately branched.

*Growth.*—Free; vigorous.

*Canes.*—Medium caliper.

*Main stems.*—Color—near Olive Green, Plate IV (R). Large prickles—many; medium length; almost straight but curved slightly downward; with narrow base of medium length; color—near Tawny-Olive, Plate XXIX (R). Small prickles—several; color—near Sayal Brown, Plate XXIX (R). Hairs—none.

*Branches.*—Color—near Spinach Green, Plate V (R). Large prickles—several, medium length, almost straight, with narrow base of medium length; color—near Dark Olive-Buff, Plate XL (R). Small prickles—several; color—near Deep Olive-Buff, Plate XL (R). Hairs—none.

*New shoots.*—Color—near Victoria Lake, Plate I (R). Large prickles—several, medium length, almost straight, with base of medium length; color—near Victoria Lake, Plate I (R), with tips of near Deep Olive-Buff, Plate XL (R). Small prickles—few. Hairs—none.

I claim:

A new and distinct variety of rose plant of the hybrid tea class, substantially as herein shown and described, characterized particularly as to novelty by the unique combination of above average vigor, a uniform and upright habit of growth, and a unique Rose Red general color tonality of the flowers, popularly described as cherry red.

No references cited.

ANTONIO F. GUIDA, *Acting Primary Examiner.*

ROBERT E. BAGWILL, *Assistant Examiner.*